(12) United States Patent
Hanin et al.

(10) Patent No.: US 7,140,371 B2
(45) Date of Patent: Nov. 28, 2006

(54) SURFACE TOPOGRAPHY METHOD FOR DETERMINING EFFECTS OF A BOTULINUM TOXIN UPON A MUSCLE AND FOR COMPARING BOTULINUM TOXINS

(75) Inventors: Lisa D. Hanin, Monroeville, PA (US); Gregory F. Brooks, Irvine, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 10/997,593

(22) Filed: Nov. 24, 2004

(65) Prior Publication Data

US 2005/0241652 A1 Nov. 3, 2005

Related U.S. Application Data

(63) Continuation-in-part of application No. 10/663,041, filed on Sep. 15, 2003, which is a continuation-in-part of application No. 10/099,602, filed on Mar. 14, 2002, now Pat. No. 6,688,311.

(51) Int. Cl.
*A61B 5/00* (2006.01)
*A61B 19/00* (2006.01)

(52) U.S. Cl. ...................... 128/898; 600/300

(58) Field of Classification Search ............... 128/898; 600/300
See application file for complete search history.

(56) References Cited

U.S. PATENT DOCUMENTS

| | | | |
|---|---|---|---|
| 3,689,638 A | 9/1972 | Piette | |
| 4,758,730 A | 7/1988 | Bazin | |
| 4,932,936 A * | 6/1990 | Dykstra et al. | 604/511 |
| 4,997,657 A | 3/1991 | Horrobin | |
| 5,183,462 A | 2/1993 | Borodic | |
| 5,437,291 A | 8/1995 | Pasricha et al. | |
| 5,512,547 A * | 4/1996 | Johnson et al. | 514/21 |
| 5,670,484 A | 9/1997 | Binder | |
| 5,714,468 A | 2/1998 | Binder | |
| 5,766,606 A | 6/1998 | Brady | |
| 5,989,545 A | 11/1999 | Foster et al. | |
| 6,063,768 A | 5/2000 | First | |
| 6,113,915 A | 9/2000 | Aoki et al. | |
| 6,139,845 A | 10/2000 | Donovan | |
| 6,143,306 A | 11/2000 | Donovan | |
| 6,261,572 B1 | 7/2001 | Donovan | |
| 6,265,379 B1 | 7/2001 | Donovan | |
| 6,506,399 B1 * | 1/2003 | Donovan | 424/423 |

(Continued)

FOREIGN PATENT DOCUMENTS

DE 19852981 A1 5/2000

(Continued)

OTHER PUBLICATIONS

Ascher et al, french translation of Botulinum Toxin in the Treatment of Frontoglabellar and Periorbital Wrinkles, Annales de Chirurgie Plastique et Esthetique, Feb. 1995, 40(1):67-76.*

(Continued)

*Primary Examiner*—Corrine McDermott
*Assistant Examiner*—Thomas J. Sweet
(74) *Attorney, Agent, or Firm*—Stephen Donovan

(57) ABSTRACT

Skin topographical methods for quantifying pharmacodynamic parameters of a paralytic effect of a Clostridial toxin, such as a *botulinum* toxin upon a muscle, such as a frontalis muscle. The methods are effective in determining the potency of a Clostridial toxin, and in comparing toxins. For example, wrinkle reduction effects caused by one or more neurotoxins may be monitored, and differences in effects correspond to differences of neurotoxins.

19 Claims, 3 Drawing Sheets

U.S. PATENT DOCUMENTS

| | | | | |
|---|---|---|---|---|
| 6,688,311 B1 * | 2/2004 | Hanin | ......................... | 128/898 |
| 6,701,171 B1 * | 3/2004 | Quistorff et al. | ............ | 600/328 |
| 2002/0064536 A1 * | 5/2002 | Hunt | ....................... | 424/247.1 |
| 2003/0118598 A1 * | 6/2003 | Hunt | ....................... | 424/184.1 |

FOREIGN PATENT DOCUMENTS

| | | |
|---|---|---|
| WO | WO9633273 | 10/1996 |
| WO | WO9807864 | 2/1998 |
| WO | WO9903483 | 1/1999 |
| WO | WO9917806 A1 | 4/1999 |
| WO | WO0010598 | 3/2000 |
| WO | WO0015245 | 3/2000 |
| WO | WO0024419 | 5/2000 |
| WO | WO0057897 | 10/2000 |
| WO | WO0062746 | 10/2000 |
| WO | WO0074703 | 12/2000 |
| WO | WO0121213 | 12/2000 |

OTHER PUBLICATIONS

Guerrisis, Jorge et al., Local Injection into Mimetic Muscles of Botulinum Toxin A for the Treatment of Facial Lines, Annals of Plastic Surgery, vol. 39, No. 5, pp. 447-453, Nov. 1997.

Hamlin, Ja et al. Serial Neurophysiological Studies of Intramuscular Botulinum-A toxin in Humans. Muscle & Nerve, pp. 1385-1392, Dec. 1994.

Koman, La et al. Spasticity Associated with Cerebral Palsy in Children, Therapy in Practice, Pediatric Drugs, 2003.

Aoki, R et al. Preclinical update on BOTOX (botulinum toxin type A)-purified neurotoxin complex relative to other botulinum neurotoxin preparations. European Journal of Neurology, vol. 6 (Suppl 4): S3-S10, 1996.

Brach, Jennifer S et al. Measuring Fatigue Related to Facial Muscle Function, Arch. Phys. Med Reabil, vol. 76, pp. 905-908, Oct. 1995.

Carruthers, J et al. Treatment of Glabellar Frown Lines with C. Botulinum-A Exotoxin, J. Dermatol Surg. Oncol. vol. 18, No. 1, pp. 17-21, Jan. 1992.

Corcuff, P et al. Skin Relief and Agin, J. Society. Cosmet. Chem, vol. 34. pp. 177-190, Jul. 1983.

Dogweiler R. Botulinum Toxin type A causes diffuse and highly selective atrophy of rat prostate. Neurourol Urodyn, vol. 17, No. 4, p. 363, 1998.

Dressler D et al., Electromyographic Quantification of the Paralysing Effect of Botulinum Toxin in the Stemocleidomastoid Muscle. European Neurology, vol. 43, pp. 13-16, 2000.

Fauci, Anthony et al. Harrison's Principles of Internal Mediciine, 14th Edition, 1998 by McGraw Hill.

Fridlund, Alan et al. Guidelines for human electromyographic research. The Socieity for Psychophysiological Research, Inc. vol. 23, No. 5, pp. 567-589, 1986.

Grove, Gary et al. Objective Methods for Assessing Skin Surface Topography Noninvasively. Cutaneous Investigation in Health and Disease, by Marcel Dekker, Inc., Chapter One, pp. 1-32, 1989.

Grove, Gary et al. Skin replica analysis of photodamaged skin after therapy with tretinoin emollient cream. Journal of the American Academy of Dermatology. vol. 25, No. 2, Part I, pp. 231-237, Aug. 1991.

Heckman, Marc et al. Quantification of the efficacy of botulinum toxin type A by digital image analysis. Journal of American Academy of Dermatology, Oct. 2001, vol. 45, pp. 508-514, published online May 23, 2001.

Johnson Eric A. Biomedical aspects of Botulinum Toxin. J. Toxicol Toxin Reviews, vol. 18, No. 1, pp. 1-15, Abstract, 1999.

Leyden, James J. et al. Treatment of photodamaged facial skin with topical tretinoin. Journal of the American Academy of Dermatology, vol. 21, No. 3, Part 2, pp. 638-644, Sep. 1989.

Pennock, Jennifer D. et al. Relationship between muscle activity of the frontalis and the associated brow displacement. Plast. Reconstr. Surg. vol. 104, No. 6, pp. 1789-1797, Nov. 1999.

Senior, Ma. Botox and the management of pectoral spasm after subpectoral implant insertion. Plast. Reconstr. Surg. vol. 106, No. 1, pp. 224-225, July 2000.

Tassinary, Louis G. et al. A psychometric study of surface electrode placements for facial electromyographic recording: I. The Brow and Cheek Muscle Regions. Pyschophysiology, vol. 26, No. 1, pp. 1-16, Abstract, 1989.

Van Boxtel, A. et al. Amplitude and Bandwidth of the Frontalis Surface EMG: Effects of Electrode parameters. Pyschophysiology, vol. 21, No. 6, pp. 699-707, Abstract, 1984.

Vitti, Mathias et al. Electromyograhpic Investigation of Procerus and Frontalis Muscles. Electromyogr. Clin. Neurophysiol. vol. 16, pp. 227-236, 1976.

Guerrisis, Jo. Injection of botulinum toxin A into orbicularis oculi muscle for the treatment of crow's feet and the discussion thereof. Plastic and Reconstructive Surgery (United States), vol. 105, No. 6, pp. 2219-2228, May 2000.

Ascher, B et al. La Toxin Botulique Dans Le Traitement Des Rides Fronto-Glabellaires et de la Region Orbitaire. Annales de Chirurgui Plastique et Esthetique, vol. 40, No. 1, pp. 67-76, Feb. 1995.

Sloop, RR et al. Dose-response curve of human extensor digitorum brevis muscle function to intramuscularly injected botulinum toxin type A, Neurology, vol. 46, No. 5, pp. 1382-1386, May 1996.

Jacobi, U et al. In vivo determination of skin surface topography using an optical 3D device. Skin Res. Technol. vol. 10, No. 4, pp. 207-214, Nov. 2004.

Blitzer et al. Journal Abstract from the Archives of Otolaryngology-Head & Neck Surgery, vol. 123, No. 4, pp. 389-392, Apr. 1997.

Pribitkin et al. Journal Abstract from the Archives of Otolaryngology-Head & Neck Surgery, vol. 123, No. 4, pp. 321-326, Apr. 1997.

* cited by examiner

SURFACE TOPOGRAPHY METHOD FOR DETERMINING EFFECTS OF A BOTULINUM TOXIN UPON A MUSCLE AND FOR COMPARING BOTULINUM TOXINS

CROSS REFERENCE

This application is a continuation-in-part of application Ser. No. 10/663,041, filed Sep. 15, 2003, which is a continuation-in-part of application Ser. No. 10/099,602, filed Mar. 14, 2002, now U.S. Pat. No. 6,688,311, the entire contents of which are incorporated herein by reference.

BACKGROUND

The present invention relates to methods for determining an effect or effects of a Clostridial toxin or toxins upon a muscle or group of muscles. In particular, the present invention relates to use of dermal topography methods for determining an effect or effects of a Clostridial toxin or toxins upon a facial muscle and for comparing multiple or different Clostridial toxins.

Movement of the face can be due to contractions of muscles underlying the skin and different muscles can move different parts of the face. For example, elevation of the brow results from contraction of the frontalis muscle. Electromyographic methods have been used to study the activity of various facial muscles. See e.g. Fridlund A. et al., *Guidelines for Human Electromyographic Research*, Psychophysiology 1986; 23(5): 567–590; Vitti M, et al., *Electromyographic Investigation of Procerus and Frontalis Muscles*, Electromyogr. clin. Neurophysiol. 1976, 16: 227–236, and; Tassinary L. et al., *A Psychometric Study of Surface Electrode Placements for Facial Electromyographic Recording: I. The Brow and Cheek Muscle Regions*, Psychophysiology 1989; 26(1): 1–16.

In particular, electromyography, including surface electromyography (sEMG) has been used to investigate activity of the frontalis muscle and resultant brow displacement. See e.g. van Boxtel A, et al., *Amplitude and bandwidth of the frontalis surface EMG: Effects of electrode parameters*, Psychophysiology 1984; 21(6): 699–707, and; Pennock J. D., et al., *Relationship between muscle activity of the frontalis and the associated brow displacement*, Plast Reconstr Surg November 1999; 104(6): 1789–1797.

Additionally, it is known to study skin topography by making a silicone rubber negative replica (a mold) of a skin surface area. The mold captures three dimensional details of the skin surface and computerized image analysis of skin line density, depths and length analysis shown can be carried out thereon. Grove, G. L., et al, *Objective method for assessing skin surface topography noninvasively*, chapter one, pages 1–32 of *Cutaneous Investigation in Health and Disease*, edited by Leveque J-L., Marcel Dekker, Inc. (1989). This method has been used to study how microfurrows on the forearm can increase in depth from about 33 Φm in children to up to about 100 Φm in the elderly. Corcuff P. et al., *Skin relief and aging*, J Soc Cosmet Chem 1983; 34:177–190. The same silicone rubber impression method has been used to examine the effect of a topical cream to treat photodamaged skin, as by reduction of periorbital (crow's feet) wrinkles. Leyden J. J., et al., *Treatment of photodamaged facial skin with topical tretinoin*, J Am Acad Dermatol 1989; 21(3) (part 2): 638–644, and; Grove G. L., et al., *Skin replica analysis of photodamaged skin after therapy with tretinoin emollient cream*, J Am Acad Dermatol 1991; 25(2) (part 1): 231–237.

*Botulinum* Toxin

The anaerobic, gram positive bacterium *Clostridium botulinum* produces a potent polypeptide neurotoxin, *botulinum* toxin, which causes a neuroparalytic illness in humans and animals known as botulism. The spores of *Clostridium botulinum* are found in soil and can grow in improperly sterilized and sealed food containers of home based canneries, which are the cause of many of the cases of botulism. The effects of botulism typically appear 18 to 36 hours after eating the foodstuffs infected with a *Clostridium botulinum* culture or spores. The *botulinum* toxin can apparently pass unattenuated through the lining of the gut and attack peripheral motor neurons. Symptoms of *botulinum* toxin intoxication can progress from difficulty walking, swallowing, and speaking to paralysis of the respiratory muscles and death.

*Botulinum* toxin type A is the most lethal natural biological agent known to man. About 50 picograms of *botulinum* toxin (purified neurotoxin complex) type A (Available from Allergan, Inc., of Irvine, Calif. under the tradename BOTOX®) is a $LD_{50}$ in mice. One unit (U) of *botulinum* toxin is defined as the $LD_{50}$ upon intraperitoneal injection into female Swiss Webster mice weighing 18–20 grams each. Seven immunologically distinct *botulinum* neurotoxins have been characterized, these being respectively *botulinum* neurotoxin serotypes A, B, $C_1$, D, E, F and G each of which is distinguished by neutralization with type-specific antibodies. The different serotypes of *botulinum* toxin vary in the animal species that they affect and in the severity and duration of the paralysis they evoke. The *botulinum* toxins apparently binds with high affinity to cholinergic motor neurons, is translocated into the neuron and blocks the release of acetylcholine.

*Botulinum* toxins have been used in clinical settings for the treatment of neuromuscular disorders characterized by hyperactive skeletal muscles. *Botulinum* toxin type A has been approved by the U.S. Food and Drug Administration for the treatment of blepharospasm, strabismus, hemifacial spasm and cervical dystonia. *Botulinum* toxin type B has also been approved by the FDA for the treatment of cervical dystonia. Clinical effects of peripheral intramuscular *botulinum* toxin type A are usually seen within one week of injection. The typical duration of symptomatic relief from a single intramuscular injection of *botulinum* toxin, type A averages about three months.

Although all the *botulinum* toxins serotypes apparently inhibit release of the neurotransmitter acetylcholine at the neuromuscular junction, they do so by affecting different neurosecretory proteins and/or cleaving these proteins at different sites. For example, *botulinum* types A and E both cleave the 25 kiloDalton (kD) synaptosomal associated protein (SNAP-25), but they target different amino acid sequences within this protein. *Botulinum* toxin types B, D, F and G act on vesicle-associated protein (VAMP, also called synaptobrevin), with each serotype cleaving the protein at a different site. Finally, *botulinum* toxin type $C_1$ has been shown to cleave both syntaxin and SNAP-25. These differences in mechanism of action may affect the relative potency and/or duration of action of the various *botulinum* toxin serotypes.

The molecular weight of the *botulinum* toxin protein molecule, for all seven of the known *botulinum* toxin serotypes, is about 150 kD. Interestingly, the *botulinum* toxins are released by Clostridial bacterium as complexes comprising the 150 kD *botulinum* toxin protein molecule along with associated non-toxin proteins. Thus, the *botulinum* toxin type A complex can be produced by Clostridial bacterium as 900 kD, 500 kD and 300 kD forms. *Botulinum* toxin types B and C, is apparently produced as only a 500 kD complex. *Botulinum* toxin type D is produced as both 300 kD and 500 kD complexes. Finally, *botulinum* toxin types E and F are produced as only approximately 300 kD complexes. The complexes (i.e. molecular weight greater than about 150 kD) are believed to contain a non-toxin hemaglutinin protein and a non-toxin and non-toxic nonhemaglutinin protein. These two non-toxin proteins (which along with the *botulinum* toxin molecule comprise the relevant neurotoxin complex) may act to provide stability against denaturation to the *botulinum* toxin molecule and protection against digestive acids when toxin is ingested. Additionally, it is possible that the larger (greater than about 150 kD molecular weight) *botulinum* toxin complexes may result in a slower rate of diffusion of the *botulinum* toxin away from a site of intramuscular injection of a *botulinum* toxin complex.

In vitro studies have indicated that *botulinum* toxin inhibits potassium cation induced release of both acetylcholine and norepinephrine from primary cell cultures of brainstem tissue. Additionally, it has been reported that *botulinum* toxin inhibits the evoked release of both glycine and glutamate in primary cultures of spinal cord neurons and that in brain synaptosome preparations *botulinum* toxin inhibits the release of each of the neurotransmitters acetylcholine, dopamine, norepinephrine, CGRP and glutamate.

*Botulinum* toxin type A can be obtained by establishing and growing cultures of *Clostridium botulinum* in a fermenter and then harvesting and purifying the fermented mixture in accordance with known procedures. All the *botulinum* toxin serotypes are initially synthesized as inactive single chain proteins which must be cleaved or nicked by proteases to become neuroactive. The bacterial strains that make *botulinum* toxin serotypes A and G possess endogenous proteases and serotypes A and G can therefore be recovered from bacterial cultures in predominantly their active form. In contrast, *botulinum* toxin serotypes $C_1$, D and E are synthesized by nonproteolytic strains and are therefore typically unactivated when recovered from culture. Serotypes B and F are produced by both proteolytic and non-proteolytic strains and therefore can be recovered in either the active or inactive form. However, even the proteolytic strains that produce, for example, the *botulinum* toxin type B serotype only cleave a portion of the toxin produced. The exact proportion of nicked to unnicked molecules depends on the length of incubation and the temperature of the culture.

It has been reported that *botulinum* toxin type A has been used in clinical settings as follows ("U" and "units" mean the same thing and a used interchangeably):

(1) about 75–250 units of BOTOX® per intramuscular injection (multiple muscles) to treat cervical dystonia;
(2) 5–10 units of BOTOX® per intramuscular injection to treat glabellar lines (brow furrows) (5 units injected intramuscularly into the procerus muscle and 10 units injected intramuscularly into each corrugator supercilii muscle);
(3) about 30–80 units of BOTOX® to treat constipation by intrasphincter injection of the puborectalis muscle;
(4) about 1–5 units per muscle of intramuscularly injected BOTOX® to treat blepharospasm by injecting the lateral pre-tarsal orbicularis oculi muscle of the upper lid and the lateral pre-tarsal orbicularis oculi of the lower lid.
(5) to treat strabismus, extraocular muscles have been injected intramuscularly with between about 1–5 units of BOTOX®, the amount injected varying based upon both the size of the muscle to be injected and the extent of muscle paralysis desired (i.e. amount of diopter correction desired).
(6) to treat upper limb spasticity following stroke by intramuscular injections of BOTOX® into five different upper limb flexor muscles, as follows:
(a) flexor digitorum profundus: 7.5 U to 30 U
(b) flexor digitorum sublimus: 7.5 U to 30 U
(c) flexor carpi ulnaris: 10 U to 40 U
(d) flexor carpi radialis: 15 U to 60 U
(e) biceps brachii: 50 U to 200 U. Each of the five indicated muscles has been injected at the same treatment session, so that the patient receives from 90 U to 360 U of upper limb flexor muscle BOTOX® by intramuscular injection at each treatment session.

It is also known that injection of a *botulinum* toxin into facial muscles can, by weakening the injected muscles, result in a decrease of hyperkinetic wrinkles in the skin overlying the paralyzed muscles. See e.g. Carruthers A. et al., *The treatment of glabellar furrows with botulinum A exotoxin*, J Dermatol Surg Oncol January 1990;16(1):83.

It is known to use a *botulinum* toxin to treat: intrathecal pain (see e.g. U.S. Pat. No. 6,113,915); paragangliomas (see e.g. U.S. Pat. No. 6,139,845); otic disorders (see e.g. U.S. Pat. No. 6,265,379); pancreatic disorders (see e.g. U.S. Pat. Nos. 6,143,306 and 6,261,572); migraine (see e.g. U.S. Patent No. 5,714,468); smooth muscle disorders (see e.g. U.S. Patent No. 5,437,291); prostate disorders, including prostatic hyperplasia (see e.g. WO 99/03483 and Doggweiler R., et al *Botulinum toxin type A causes diffuse and highly selective atrophy of rat prostate*, Neurourol Urodyn 1998; 17(4):363); autonomic nerve disorders, including hyperplasic sweat glands (see e.g. U.S. Pat. No. 5,766,606); wound healing (see e.g. WO 00/24419); reduced hair loss (see e.g. WO 00/62746); skin lesions (see e.g. U.S. Pat. No. 5,670,484), and; neurogenic inflammatory disorders (see e.g. U.S. Pat. No. 6,063,768).

Additionally it has been disclosed that targeted *botulinum* toxins (i.e. with a non-native binding moiety) can be used to treat various conditions (see e.g. U.S. Pat. No. 5,989,545, as well as WO 96/33273; WO 99/17806; WO 98/07864; WO 00/57897; WO 01/21213; WO 00/10598.

A *botulinum* toxin has been injected into the pectoral muscle to control pectoral spasm. See e.g. Senior M., *Botox and the management of pectoral spasm after subpectoral implant insertion*, Plastic and Recon Surg, July 2000, 224–225.

Both liquid stable formulations and pure *botulinum* toxin formulations have been disclosed (see e.g. WO 00/15245 and WO 74703) as well as topical application of a *botulinum* toxin (see e.g. DE 198 52 981).

Typically, a Clostridial toxin, such as a *botulinum* toxin, is administered locally and directly into a target tissue, such as a skeletal muscle, by intramuscular or subcutaneous injection. Entry of a Clostridial toxin into the circulatory system is undesirable, since botulism or tetanus can result. Additionally, entry of a Clostridial toxin into the systemic circulation typically results in generation of antibodies against the toxin. The presence of antibodies leads to a loss or diminishment of a desired clinical response, such as a muscle paralysis. Thus, methodologies for determination of bioavailability of a Clostridial toxin practiced in regard to an intravenously or orally administered pharmaceutical are neither relevant nor applicability with regard to a locally (i.e. intravenous or subcutaneous) administered Clostridial toxin.

Unfortunately, therefore methodologies which examine a physiological fluid (i.e. blood, urine) are of little or no value to determine bioavailability of a Clostridial toxin to a target muscle or muscle group, due to the local (non-systemic) administration and effect of the toxin. Thus, currently available analytical techniques used to perform classical absorption, distribution, biotransformation and elimination studies on an oral or intravenously administered drugs cannot be used.

Botulinum toxin has been injected into facial muscles, such as the orbicularis oculis, corrugator supercilii and frontalis muscles for the cosmetic purpose of reducing certain facial wrinkles, and it is known to use electromyographic and/or photographic techniques to assess the efficacy of such injections. Guerrissi J. et al., *Local injection into mimetic muscles of botulinum toxin A for the treatment of facial lines*, Ann Plast Surg 1997;39(5):447–53. Electromyography has also been used to assess the effect of injection of a *botulinum* toxin into the sternocleidomastoid muscle for treatment of cervical dystonia. Dressler D. et al., *Electromyographic quantification of the paralysing effect of botulinum toxin in the sternocleidomastoid muscle*, Eur Neurol 2000; 43: 13–16. In sEMG the surface electrodes are placed at fixed distances from the injection point, typically 1 cm and 3 cm from the injection point. The surface electrodes can be used to measure the amplitude and area of a compound muscle action potential (CMAP) during maximal voluntary contraction of the injected muscle. One expects to find that CMAP decreases with the onset of muscle paralytic effect and increases as the paralytic effect wears off.

Unfortunately, electromyographic methods for determining an effect of a Clostridial toxin, such as a *botulinum* toxin, upon a muscle or muscle group can be unsatisfactory because of the variability of electrical activity from a particular muscle between patients an even with the same patient in different positions or on different days due to the known vagaries of electrophysiology. For example, repeat surface electromyographic recordings can show significant (i.e. from about 7% to about 20%) variability when taken from the same patient at the same time. Additionally, the extent of maximal voluntary contraction, at which the sEMG recording is taken, can be variable between and among patients.

Photographic methods, such as digital image analysis, have been used to determine efficacy of a *botulinum* toxin to treat hyperkinetic facial lines. Heckmann M., et al., *Quantification of the efficacy of botulinum toxin type A by digital image analysis*, J Am Acad Dermatol 2001; 45: 508–514. As with electromyographic methods, photographic methods also show significant intra and inter subject variability. Thus, photographic methods for determining an effect of a Clostridial toxin, such as *botulinum* toxin, upon a muscle or a muscle group can lack precision and accuracy and the quality and value of the images obtained are as variant as the lighting conditions, type of film used, film speed and the film development process used.

Thus both electromyographic and photographic methods for assessing an effect of a *botulinum* toxin upon a muscle have significant drawbacks and deficiencies, and neither of these methods can readily provide a three dimensional permanent record amenable to analysis.

Botulinum Toxin Lethality Assay

The *botulinum* toxin lethality assay involves the injection of a *botulinum* toxin composition intraperitoneally into a mouse. For example, the assay may include injecting intraperitoneally (IP) a desired amount of BOTOX® or DYSPORT® into a mouse. Several days after the injection, the injected mice are assessed for mortality. The potency of the product is related to the amount of *botulinum* toxin that is required to kill 50% of the injected mice ($LD_{50}$).

Contrary to general belief, the mouse unit (i.e., the amount of *botulinum* toxin that equals the $LD_{50}$) is not a standardized unit. It is well documented that the assay to determine the potency of *botulinum* toxin type A in mouse $LD_{50}$ units is prone to significant inter-laboratory variability (Schantz and Kautter, *J Ass of Anal Chem* 1978, 61:96–99). One study designed to standardize a *Botulinum* type A toxin assay involved 11 different laboratories (Sesardic et al, *Pharacol Toxico* 1996, 78:283–288). In this study there was found to be up to a 10-fold difference in results. This variability in mouse $LD_{50}$ is not unique to assays involving *botulinum* toxin. In fact, because of the variability of this assay, a number of regulatory agencies have abandoned requiring the routine use of $LD_{50}$ for toxicity testing for a number of chemicals, solvents, cosmetics and drugs (Pearce et al, *Toxicol App Pharm* 1994, 128:69–77; U.S. Pat. Nos. 5,401,243 and 5,183,462,).

In addition, although BOTOX® and DYSPORT® are both *botulinum* toxin type A-containing compositions, BOTOX® has a greater potency than DYSPORT® when therapeutically assessed. However, when measuring the potency of BOTOX® and DYSPORT® using the lethality assay described above, BOTOX® and DYSPORT® exhibit similar potencies.

The expanding medical importance of *botulinum* toxins has increased the need for, and placed a premium on, the precise analysis of biological activity contained in preparations of *botulinum* toxin type A for both clinical use and laboratory investigation.

What is needed therefore is a non-invasive method for determining a pharmacodynamic effect (such as a muscle paralytic effect) of a Clostridial toxin, such as a *botulinum* toxin, upon a muscle or muscle group, which method provides an accurate and precise three dimensional record amendable to computerized analysis. There also remains a need for a non-invasive and non-lethal methods for determining the potency of a Clostridial toxin, and for methods of comparing neurotoxins.

SUMMARY

The present invention addresses these needs and provides non-invasive methods for determining a pharmacodynamic effect (such as a muscle paralytic effect) of a Clostridial toxin, such as a *botulinum* toxin, upon a muscle or muscle group. Additionally, the method provides an accurate and precise three dimensional record amendable to computerized analysis. The method disclosed herein can comprise the steps of administering a Clostridial toxin to a muscle; making an impression of a feature of a skin surface in proximity to the muscle to which the Clostridial toxin was administered; examining the impression, and; determining onset of paralysis, peak paralysis and duration of paralysis of the muscle by the Clostridial toxin.

In one embodiment of the present methods, a method for determining the potency of a *botulinum* neurotoxin, comprises examining a muscle of an individual at a maximum voluntary contraction; administering a composition comprising a *botulinum* neurotoxin to the muscle; and examining the muscle after the muscle has been administered the *botulinum* neurotoxin without killing the individual to determine an effect of the *botulinum* neurotoxin on the muscle.

This method provides a non-invasive approach to determine the potency of one or more *botulinum* neurotoxins.

In another embodiment, a method for comparing multiple *botulinum* neurotoxins, generally comprises comparing wrinkle reducing effects of two or more neurotoxins, such as *botulinum* neurotoxins. For example, the method may comprise measuring a reduction of a skin wrinkle of an individual resulting from administration of a first *botulinum* neurotoxin in the vicinity of a muscle in proximity to the skin wrinkle. The method also includes measuring a reduction of a skin wrinkle of an individual resulting from administration of a second *botulinum* neurotoxin in the vicinity of a muscle in proximity to the skin wrinkle. The reductions may be compared to determine a difference between the first *botulinum* neurotoxin and the second *botulinum* neurotoxin. The individual may be the same person and the neurotoxin may be administered to two regions of that person, or the individuals may be different people.

In a more specific embodiment, a method for comparing *botulinum* neurotoxins, comprises: making a first impression of a skin surface region of an individual in proximity to a first muscle and a second muscle into or in the vicinity of which a first *botulinum* neurotoxin and a second *botulinum* neurotoxin, respectively are to be administered. The impression is made while the first and second muscles are at a first maximum voluntary contraction. The method also comprises administering the first and second *botulinum* toxins to the first and second muscles, respectively. A second impression is made of the skin surface region in proximity to the first and second muscles while the first and second muscles are at a second voluntary contraction. The first and second impressions are examined, and a mean depth of the skin wrinkle, among other things, may be obtained. The mean depth of the skin wrinkle is then compared to determine differences between the first and second neurotoxins.

Thus, in general, a method for comparing *botulinum* neurotoxin-containing compositions may comprise the steps of: examining a first superficial body region and a second superficial body region of an individual. The first and second superficial body regions typically comprise at least a portion of a muscle. The examination occurs while the muscle is at a maximum voluntary contraction. The method also comprises administering a first *botulinum* neurotoxin-containing composition to the first region, and administering a second *botulinum* neurotoxin-containing composition to the second region. After administration of the first composition, the first region is examined, and after administration of the second composition, the second region is examined. The examinations are effective in determining one or more effects of the compositions. A difference in the effects corresponds to a difference in the first composition and the second composition.

The administering of the Clostridial toxin or toxins in the present methods can be carried out by intramuscular injection or subcutaneous injection of the Clostridial toxin or toxins. Alternately, a suitable controlled release implant, containing a Clostridial toxin or toxins, can be inserted under the skin or within the muscle. Preferably, the muscle is a facial muscle (such as a frontalis muscle) because facial skin can show a more determinable response to injection of a Clostridial toxin into the muscle which underlies the skin. In other words, the skin of the face such as on the forehead has a topography which encompasses easily discernable wrinkles, furrows and lines which can produce a quantifiable response to an intramuscular toxin injection. Thus, a causal connection exists between the paralytic effect of a Clostridial toxin upon a muscle and change in facial topography. It has been discovered how to quantify this causality so as to determine pharmocodynamic effects of a Clostridial toxin upon muscles.

Preferably, the Clostridial toxin is a *botulinum* toxin (such as a *botulinum* toxin type A, B, C, D, E, F or G). Several *botulinum* toxins are commercially available and have been used clinically to paralyze various muscles. An embodiment of the present invention encompasses use of from about 1 unit to about 1,000 units of a *botulinum* toxin type A (i.e. between about 1–300 units of the BOTOX® type A *botulinum* toxin or between about 1–1000 units of the DYSPORT® type A *botulinum* toxin); 10 to 10,000 units of a type B *botulinum* toxin (such as the MYOBLOC type B *botulinum* toxin), and; amounts of the other *botulinum* toxins based on their known differing potencies.

An impression step of the present methods can comprise applying a polymeric material to the skin surface to thereby obtain a mold which has, on the surface of the mold in contact with the skin surface, a negative replica of a skin surface topography. The examining step can comprise illuminating the negative replica surface of the mold with incident light.

Additionally, a determining step of the present methods can further comprise determining an extent of a diffusion of the Clostridial toxin in the muscle to which the Clostridial toxin was administered and into a surrounding area. And the determining step can comprise, subsequent to the illuminating step, the step of generating an optical image of the illuminated negative replica surface. Furthermore, the determining step can comprise, subsequent to the generating step, the step of computing a parameter of a skin line present on the negative replica surface The route of administration and amount of Clostridial toxin administered can vary widely according to the particular muscle being injected and various patient variables including size, weight, age, disease severity and responsiveness to therapy. Methods for determining the appropriate route of administration and dosage are generally determined on a case by case basis by the attending physician. Such determinations are routine to one of ordinary skill in the art (see for example, *Harrison's Principles of Internal Medicine* (1997), edited by Anthony Fauci et al., $14^{th}$ edition, published by McGraw Hill). Treatment is carried out so as to substantially avoiding entry of the toxin into the systemic circulation (i.e. by use of subcutaneous or intramuscular injection as opposed to intravenous administration).

The specific dosage appropriate for administration is readily determined by one of ordinary skill in the art according to the factors discussed above. The dosage can also depend upon the size of the muscle to be treated or denervated, and the commercial preparation of the toxin. Generally, it is known that the amount of a Clostridial toxin (such as a *botulinum* toxin) to be injected is proportional to the mass and level of activity of the muscle tissue to be treated.

The present invention includes within its scope the use of any Clostridial toxin which has a long duration therapeutic effect. For example, neurotoxins made by any of the species of the toxin producing *Clostridium* bacteria, such as *Clostridium botulinum, Clostridium butyricum*, and *Clostridium beratti* can be used or adapted for use in the methods of the present invention. Additionally, all of the *botulinum* serotypes A, B, C, D, E, F and G can be advantageously used in the practice of the present invention, although type A is the most preferred serotype, as explained above.

Definitions

As used herein, "Clostridial neurotoxin" means a neurotoxin produced or obtained from, or native to, a Clostridial bacterium, such as *Clostridium botulinum, Clostridium butyricum* or *Clostridium beratti*, as well as a Clostridial neurotoxin made recombinantly by a non-Clostridial species.

As used herein, "*botulinum* toxin" means a neurotoxin produced by or obtained from *Clostridium botulinum* bacteria, as well as a *botulinum* toxin (or the light chain or the heavy chain thereof) made recombinantly by or obtained from a non-Clostridial species. The phrase "*botulinum* toxin", as used herein, encompasses the *botulinum* toxin serotypes A, B, C, D, E, F and G. *Botulinum* toxin, as used herein, also encompasses both a *botulinum* toxin complex (i.e. the 300, 600 and 900 kDa complexes) as well as the purified *botulinum* toxin (i.e. about 150 kDa). "Purified *botulinum* toxin" is defined as a *botulinum* toxin that is isolated, or substantially isolated, from other proteins, including proteins that form a *botulinum* toxin complex. A purified *botulinum* toxin may be greater than 95% pure, and preferably is greater than 99% pure. The *botulinum* $C_2$ and $C_3$ cytotoxins, not being neurotoxins, are excluded from the scope of the present invention. The *botulinum* toxin can be present as a *botulinum* toxin complex (i.e. as an approximately 300 to about 900 kiloDalton complex depending upon the particular *botulinum* toxin serotype) or the *botulinum* toxin can be is present as a pure or purified *botulinum* toxin (i.e. as the *botulinum* toxin molecule of about 150 kiloDaltons).

As used herein, "modified *botulinum* toxin" refers to a *botulinum* toxin that has had at least one of its amino acids deleted, modified, or replaced, as compared to a native *botulinum* toxin. Additionally, the modified *botulinum* toxin can be a recombinantly produced neurotoxin, or a derivative or fragment of a recombinantly made neurotoxin. A modified *botulinum* toxin retains at least one biological activity of the native *botulinum* toxin, such as, the ability to bind to a *botulinum* toxin receptor, or the ability to inhibit neurotransmitter release from a neuron. One example of a modified *botulinum* toxin is a *botulinum* toxin that has a light chain from one *botulinum* toxin serotype (such as serotype A), and a heavy chain from a different *botulinum* toxin serotype (such as serotype B). Another example of a modified *botulinum* toxin is a *botulinum* toxin coupled to a neurotransmitter, such as substance P.

As used herein, "polysaccharide" means a polymer of more than two saccharide molecule monomers, which monomers can be identical or different.

As used herein, "protein stabilizer" (or "primary stabilizer") is a chemical agent that assists to preserve or maintain the biological structure (i.e. the three dimensional conformation) and/or biological activity of a protein (such as a Clostridial neurotoxin, such as a *botulinum* toxin). Stabilizers can be proteins or polysaccharides. Examples of protein stabilizers include hydroxyethyl starch (hetastarch), serum albumin, gelatin, collagen, as well as a recombinant albumin, gelatin or collagen. As disclosed herein, the primary stabilizer can be a synthetic agent that would not produce an immunogenic response (or produces an attenuated immune response) in a subject receiving a composition containing the primary stabilizer. In certain embodiments, the protein stabilizers may be proteins from the same species of animal that is being administered the protein. Additional stabilizers may also be included in a pharmaceutical composition. These additional or secondary stabilizers may be used alone or in combination with primary stabilizers, such as proteins and polysaccharides. Exemplary secondary stabilizers include, but are not limited to non-oxidizing amino acid derivatives (such as a tryptophan derivate, such as N-acetyl-tryptophan ("NAT")), caprylate (i.e. sodium caprylate), a polysorbate (i.e. P80), amino acids, and divalent metal cations such as zinc. A pharmaceutical composition can also include preservative agents such as benzyl alcohol, benzoic acid, phenol, parabens and sorbic acid. A "recombinant stabilizer" is a "primary stabilizer" made by recombinant means, such as for example, a recombinantly made albumin (such as a recombinantly made human serum albumin), collagen, gelatin or a cresol, such as an M-cresol.

"Local administration" means direct injection of the Clostridial into the muscle, subcutaneous or intradermal injection. Systemic routes of administration, such as oral and intravenous routes of administration, are excluded from the scope of the present invention.

The Clostridial toxin (such as a *botulinum* toxin) used in the present invention can be a modified Clostridial toxin, that is the toxin can have at least one of its amino acids deleted, modified or replaced, as compared to a native Clostridial toxin. Thus, the Clostridial toxin used can be a recombinantly produced Clostridial (e.g. *botulinum*) toxin or a derivative or fragment thereof. A *botulinum* toxin used in a method according to the present invention is a *botulinum* neurotoxin. *Botulinum* toxins which are not neurotoxins (such as the *botulinum* toxins types $C_2$ and $C_3$) are not used in a method within the scope of the present invention.

Each and every feature described herein, and each and every combination of two or more of such features, is included within the scope of the present invention provided that the features included in such a combination are not mutually inconsistent. In addition, any feature or combination of features may be specifically excluded from any embodiment of the present invention.

Additional aspects and advantages of the present invention are set forth in the following description and claims, particularly when considered in conjunction with the accompanying drawings.

DRAWINGS

DESCRIPTION

Figure 1:
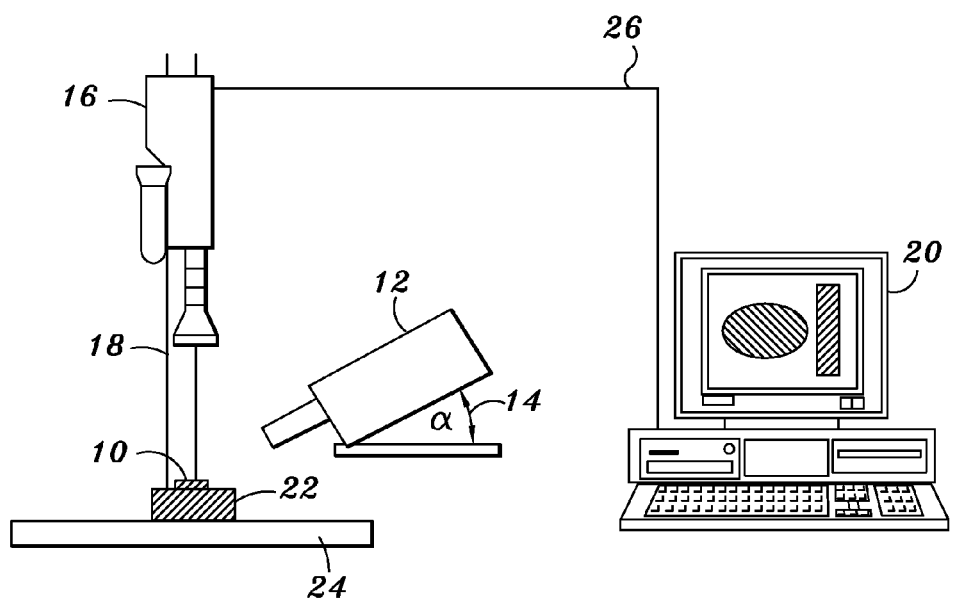
FIG. 1 is a diagrammatic illustration of a digital imaging system for use in a method of the present invention.

The present invention is based upon the discovery that a skin surface topographical method can be used to determine an effect of a Clostridial toxin or Clostridial neurotoxin upon a muscle. For example, the effect determined through use of the disclosed method can be a paralytic effect (i.e. inability to contract), including onset of effect, peak effect and duration of paralytic effect of a Clostridial toxin upon a muscle. Or, the effect determined may be a reduction in one or more characteristics of a wrinkle or wrinkles, or the effect may be one or more differences among neurotoxins. The skin surface topographical method can be practiced by making silicone rubber negative replicas of a skin surface area before and after administration of a Clostridial toxin to a muscle or muscle group of an individual patient. Imaging profile analysis of the skin surface replica may then be carried out.

The present methods may be effective in determining one or more effects of Clostridial neurotoxins. For example, the present methods may be effective in determining the potency of a Clostridial neurotoxin, such as a *botulinum* toxin. Currently, the potency of *botulinum* toxin is determined using the mouse lethality assay, as understood by persons of ordinary skill in the art. In addition, the present methods may be effective in comparing multiple Clostridial neurotoxins, such as *botulinum* neurotoxins. For example, the methods may be effective in determining whether a particular *botulinum* neurotoxin is more potent, more safe, has a longer duration of effectiveness or has a different antibody response than one or more other neurotoxins. Advantageously, the present methods enable the potency and other characteristics of neurotoxins to be determined and/or compared without injuring or killing the subject who is administered the toxin or toxins. The present methods also provide more meaningful information or results regarding potency, bioavailability, and the like compared to the mouse lethality assay that is currently used.

Previously, skin surface topography methods have been used to assess development of microfurrows in the skin with age, and the efficacy of topically applied creams to treat photodamaged skin. Surprisingly, it has now been discovered that skin topography can be used to assess an effect of a Clostridial neurotoxin, such as a *botulinum* toxin, upon a muscle, and to compare the effects and properties of multiple neurotoxins, such as *botulinum* neurotoxins.

The present methods employ skin topography to determine the parameters of a muscle weakening effect or effects of an intramuscular administration, such as a intramuscular or subdermal injection, of a Clostridial neurotoxin, such as a *botulinum* toxin, into a muscle, such as the frontalis muscle. Thus, by practicing the present methods, skin topography is used to determine, subsequent to injection of a Clostridial toxin, that the injected toxin produces a dose-dependent inhibition of maximum voluntary contraction of a facial muscle, such as the frontalis muscle. The present methods thereby provide a way of using facial topography to determine an effect of administration of a Clostridial toxin. Or, stated differently, the present methods can be used to determine the potency of a Clostridial neurotoxin, such as a *botulinum* toxin. Importantly, the potency of the neurotoxin can be determined without killing an individual.

In one embodiment, a method makes use of the known antiwrinkling effect of a Clostridial toxin, such as a *botulinum* toxin, as determined from a quantitative facial topography analysis, to quantify various pharmacodynamic and/or neurophysiological properties (profile) of the toxin following intramuscular or subcutaneous injection, into a muscle, such as the frontalis muscle of the forehead. The present methods permit quantification of onset of muscle paralytic effect, peak paralytic effect and duration of the paralytic effect. The purpose of the methods is not to determine if or to what extent a Clostridial toxin has an antiwrinkling effect upon intramuscular injection of the toxin.

In another embodiment, a method for quantitative assessment of the effect of a Clostridial toxin on muscle activity uses: (1) a skin surface topography profile; (2) a photographic eyebrow position assessment, and/or; (3) an examination of underlying muscle activity (sEMG).

In the practice of the present methods, a skin surface topography procedure is used to make skin surface replicas for the purpose of evaluating a muscle weakening effect of a Clostridial toxin, such as a *botulinum* toxin, on a muscle, such as the frontalis muscle, following i.e. maximum voluntary contraction of the muscle.

Additionally, a muscle weakening effect of an administered Clostridial toxin upon a muscle, can be determined according to the disclosure herein, where the muscle is the frontalis muscle, by quantifying eyebrow displacement. It has been discovered that a geometric facial measurement of eyebrow mobility provides for an objective description and evaluation of the effect of a Clostridial toxin on the frontalis muscle. This is achieved by measurements of brow position taken from standardized serial photographs. The digital images are analyzed by software measuring the distance between the inner canthus of the eye and the lower edge of the eyebrow. Graded, sustained frontalis muscle activity correlates with graded, sustained elevation of the eyebrow.

Furthermore, the present invention encompasses use of a relationship between frontalis muscle activity, as measured with sEMG, and the associated eyebrow displacement. Measurements by maximum static response assay can be analyzed. Thus individuals are asked to elevate their eyebrows and to view the electromyographic signal to maintain voluntary contractions for 5 seconds at maximum level. The present invention with regard to this methodology is to use the known sEMG method to analyze brow displacement as another measure of frontalis muscle activity for the purpose of determining an effect of a Clostridial toxin. Electrophysiological measurements can be used to more directly assess muscle activity and the pharmacodynamic properties of a Clostridial toxin, such as a *botulinum* toxin. Analysis of surface electromyographical (sEMG) activity of the frontalis muscle can be carried out.

In view of the disclosure herein, it may be understood that a method for determining the potency of a Clostridial neurotoxin, such as a *botulinum* neurotoxin, broadly comprises a step of administering the neurotoxin to an individual, such as a person, and determining an effect of the neurotoxin on the individual without killing the individual. Preferably, the individual is a human.

In a particular embodiment, a method for determining the potency of a *botulinum* neurotoxin comprises a step of examining a muscle of an individual at a maximum voluntary contraction. After such examination, the method comprises administering a composition comprising a *botulinum* neurotoxin to the muscle. After the administration of the composition, the muscle is examined again to determine the effect of the *botulinum* neurotoxin on the muscle. In comparison to the mouse lethality assay, the method is practiced without killing the individual.

The method may be practiced and the potency more accurately determined by repeating the steps of the foregoing method for a plurality of individuals, such as two or more individuals. Increasing the number of individuals for the method may help provide more accurate determination of the potency, and reduce errors in measurements. The method may also comprise a step of analyzing the effect of the *botulinum* neurotoxin on the muscle as a function of amount of the *botulinum* toxin in the composition or the amount of neurotoxin administered to the individual, for each individual administered the composition. Thus, by practicing the present method, it is possible to obtain dose-response data associated with the *botulinum* neurotoxin in order to determine the potency of the toxin. For example, the potency may be related to the amount of *botulinum* neurotoxin that provides an effect, such as muscle paralysis, that is about 50% that of the maximum muscle paralysis.

Preferably, the muscles are examined by one or more surface topography techniques, as disclosed herein, such as by examining the change or reduction in a wrinkle associated with the muscle contraction, by examining a sEMG record or records, and examining a photograph or photographs of wrinkles associated with the muscle contraction.

The present methods also encompass methods for comparing *botulinum* neurotoxins, or *botulinum* neurotoxin-containing compositions. Or, stated differently, the methods may be practiced to distinguish *botulinum* neurotoxins, such as *botulinum* neurotoxins of different serotypes, *botulinum* neurotoxins of the same serotype but different strains, and/or *botulinum* neurotoxins that have been modified or altered.

In short, a reduction in a characteristic of a skin wrinkle caused by administration of a neurotoxin can be compared to a reduction of the same characteristic of a skin wrinkle caused by administration of a different neurotoxin. By comparing how different neurotoxins reduce wrinkles, one can determine potency, safety, effectiveness, and antibody response to the neurotoxins. Wrinkle characteristics that may be reduced and compared include wrinkle depth, wrinkle length, wrinkle width, wrinkle surface area, number of wrinkles, wrinkle density, and the like.

For example, a method for comparing *botulinum* neurotoxin-containing compositions may comprise examining a first superficial body region and a second superficial body region of an individual. The first and second superficial body regions typically comprise at least a portion of a muscle. As used herein, a superficial body region refers to a region of an individual's body that exhibits a visual effect or response from contraction or relaxation of a muscle. Thus, the superficial body regions typically refer to regions of the body including the skin surface of an individual, and typically include one or more wrinkles. The superficial body region or regions may be located on an individual's head, such as face or forehead, and the like, or on an individual's upper torso, such as the chest, back, arms, or stomach region, or on an individual's lower torso, such as the legs and feet. In certain situations, the superficial body region is relatively thin, for example, the thickness of the region, including the muscle, is less than other portions of an individual's body.

The first superficial body region and the second superficial body region may be the same regions on opposite sides of the individual's body. For example, the first superficial body region may be located on a person's left arm, and the second superficial body region may be located on the person's right arm. Or, the first superficial body region may be located above a person's left eye, and the second superficial body region may be located above the person's right eye. Thus, the first and second superficial body regions may be located bilaterally on the individual, i.e., on opposite sides of a person's midline.

The first superficial body region and the second superficial body region may be the same location on two different individuals. For example, the first superficial body region may be located on the left corner of a person's mouth, and the second superficial body region may be located on the left corner of a different person's mouth. Or, the first superficial body region may be located on a person's neck, and the second superficial body region may be located at the same location on a different person's neck.

Or, the first superficial body region and the second superficial body region may be the same location on the same individual, but at different time points, as discussed herein.

Preferably, the first superficial body region and the second superficial body region are examined while the muscle is at a maximum voluntary contraction. A first *botulinum* neurotoxin-containing composition may then be administered to the first region, and a second *botulinum* neurotoxin-containing composition may be administered to the second region. The compositions are administered such that the neurotoxin provides a paralytic effect of a muscle in proximity to the first and second regions. The compositions may be injected, using a needle or a needleless syringe, and the compositions may be delivered subcutaneously or intramuscularly, as discussed herein. The administration of the compositions may be at substantially the same time, for example, during a single appointment or meeting with a physician, or the administration of the first and second compositions can occur at different times. In certain embodiments, such as an embodiment where the second composition is administered to a second superficial body region that is at the same location as the first superficial body region, the second composition is administered after the effects of the first composition have worn off. For example, after the muscle of the first superficial body region is no longer paralyzed.

After the first superficial body region is administered the first composition, the first superficial body region may be examined while the muscle of the first superficial body region is at a maximum voluntary contraction. The muscle is examined to determine an effect of the first composition on the first superficial body region. After the second superficial body region is administered the second composition, the second superficial body region may be examined while the muscle of the second superficial body region is at a maximum voluntary contraction to determine an effect of the second composition on the second superficial body region. A difference in effects between the neurotoxins corresponds to a difference in the first composition and the second composition.

The examining steps of the method may include one or more of the surface topographical techniques disclosed herein. For example, the examining may occur by forming an impression or mold of the superficial body regions before and after administration of the compositions. In addition, the examining may occur by electrophysiologically recording the muscle activity of the superficial body regions before and after administration of the compositions. In addition, the examining may occur by comparing photographs of the superficial body regions before and after administration of the compositions.

The method may be effective in comparing two or more different *botulinum* neurotoxins, or two or more compositions comprising a *botulinum* neurotoxin. In certain embodiments, the *botulinum* neurotoxin of the first composition is different than the *botulinum* neurotoxin of the second composition. For example, the *botulinum* neurotoxin of the first composition may be a *botulinum* neurotoxin selected from the group consisting of *botulinum* neurotoxin types A, B, C, D, E, F, and G, and the *botulinum* neurotoxin of the second composition may be a *botulinum* neurotoxin other than the *botulinum* neurotoxin of the first composition. Or, stated differently, the *botulinum* neurotoxin of the compositions may be different serotypes of *botulinum* neurotoxins. In one embodiment, the *botulinum* neurotoxin of the first composition is a *botulinum* toxin type A, and the *botulinum* neurotoxin of the second composition is a *botulinum* toxin type B. For example, the method may be used to compare BOTOX® (*botulinum* toxin type A) and MYOBLOC (*botulinum* toxin type B).

In other embodiments, the *botulinum* neurotoxin of the first composition is a *botulinum* neurotoxin produced by a first strain of a Clostridial bacteria, and the *botulinum* neurotoxin of the second composition may be a *botulinum* neurotoxin produced by a strain of Clostridial bacterial other than the first strain. Stated differently, the method may be practiced by administering two or more different strains of *botulinum* neurotoxin, which may or may not be of the same serotype. For example, the first composition may be the composition sold under the tradename, BOTOX®, and the second composition may be the composition sold under the tradename, DYSPORT®.

In another embodiment, the *botulinum* neurotoxin of the first composition may be a native *botulinum* neurotoxin obtained from a Clostridial bacteria, and the *botulinum* neurotoxin of the second composition may be a modified or altered *botulinum* neurotoxin. For example, the method may be used to compare a *botulinum* neurotoxin complex (such as BOTOX®) and a purified *botulinum* neurotoxin, available from Merz (NT201).

Thus, the present invention encompasses use of topographical, electrophysiological and/or photographical image methods as a means of measuring the muscle weakening effect of a Clostridial toxin (such as a *botulinum* toxin) to a muscle (such as the frontalis muscle), thereby providing a better understanding of the pharmacodynamic properties of Clostridial toxins. The methods may be used to effectively compare multiple neurotoxins, and to determine the potency of one or more neurotoxins.

In certain neurotoxin-containing compositions, a stabilizer is provided in an amount effective in stabilizing the neurotoxin. In publicly available *botulinum* neurotoxin-containing compositions, such as BOTOX®, human serum albumin is provided in a stabilizing amount.

In the present methods, the *botulinum* neurotoxin-containing compositions may comprise a stabilizer other than human serum albumin. For example, the compositions may comprise a polysaccharide, such as a hetastarch; a recombinantly produced albumin; a gelatin, and the like. The present methods thus may be effective in comparing *botulinum* neurotoxin-containing compositions such as a first composition which comprises a stabilizing amount of a polysaccharide, and a second composition which is substantially free of the polysaccharide; or a first composition which comprises a stabilizing amount of recombinant albumin and a second composition which is substantially free of recombinant albumin; or a first composition which comprises a stabilizing amount of gelatin, and a second composition which is substantially free of gelatin; or a first composition which comprises a stabilizing amount of human serum albumin, and a second composition comprising a stabilizer other than human serum albumin. Examples of potential compositions useful in the present methods include the compositions disclosed in U.S. Patent Publication Nos. 2003-0138437 and 2003-0118598.

In accordance with the disclosure herein, the examining steps of the foregoing methods may comprise at least one of (i) evaluating skin topography of the first and second regions; (ii) evaluating a surface electromyograph recording of the first and second regions; and (iii) evaluating photographs of the first and second regions. In certain embodiments, the examining steps comprise all three of the foregoing evaluation steps.

As discussed herein, the step of evaluating skin topography may comprise producing an impression or mold of the skin topography of the first and second regions before administration of the first and second compositions, respectively, and producing an impression of the skin topography of the first and second regions after administration of the first and second compositions, respectively.

The present methods provide a safe, convenient, and effective way of distinguishing *botulinum* neurotoxins. The difference in effects of the neurotoxins as seen with the present methods may correspond to a difference in the *botulinum* neurotoxin-containing compositions or the neurotoxins themselves, such as potency, safety, duration of effectiveness, and antibody response, among others.

In view of the disclosure herein, a method of comparing *botulinum* neurotoxins or comparing effects caused by *botulinum* neurotoxins may comprise measuring a skin wrinkle at a location or region of an individual or measuring or otherwise quantifying one or more characteristics of such a skin wrinkle or skin wrinkles, administering a *botulinum* neurotoxin to a muscle in proximity to the skin wrinkle to reduce the wrinkle, and measuring the skin wrinkle at the location after administration of the *botulinum* neurotoxin. The method may be repeated for a second *botulinum* neurotoxin or a second composition containing a *botulinum* neurotoxin at the same location on the opposite side of a person's body, such as on the opposite side of the midline of the person's body. Or the method may be repeated for a second *botulinum* neurotoxin after the effects of the first *botulinum* neurotoxin have worn off. Or, the method may be repeated by administering a second *botulinum* neurotoxin at the same location of a different individual. Thus, two or more *botulinum* neurotoxins may be compared and/or distinguished by measuring changes in the wrinkle reduction associated with administration of a *botulinum* toxin.

In one embodiment, a method for comparing *botulinum* neurotoxins comprises making a first impression of a skin surface region of an individual in proximity to a first muscle and a second muscle into or in the vicinity of which a first *botulinum* neurotoxin and a second *botulinum* neurotoxin, respectively are to be administered. The impression is made while the first and second muscles are at a first maximum voluntary contraction. The first and second *botulinum* toxins are then administered to the first and second muscles, respectively. After administration of the *botulinum* toxins, a second impression of the skin surface region is made while the first and second muscles are at a second maximum voluntary contraction. The first and second impressions are then examined and a skin wrinkle measurement is obtained. Examples of skin wrinkle measurements include wrinkle depth, such as the mean depth of the skin wrinkle, wrinkle length, such as the mean length of a skin wrinkle, the total length of a skin wrinkle, wrinkle number, such as the total number of skin wrinkles, and skin wrinkle surface area. One or more differences in a skin wrinkle measurement corresponds to a difference in the neurotoxins. For example, a difference in wrinkle number for prolonged periods of time between two different neurotoxins may be indicative of one neurotoxin having a greater duration efficacy than another neurotoxin. Or, a difference in wrinkle depth may be indicative that one neurotoxin is more potent than the other neurotoxin, assuming that substantially equal amounts of the neurotoxins were administered to the individual. The method may also comprise obtaining from the impressions a form factor skin surface characteristic. The comparing step of the foregoing method may comprise determining a paralytic effect of the first and second *botulinum* neurotoxins upon the muscles.

As discussed herein, the first and second *botulinum* neurotoxins may be different. For example, the neurotoxins may be of different serotypes. Or, the neurotoxins may be of the same serotype, but obtained from different strains of Clostridial bacteria. Or, the neurotoxins may be obtained using different production methods, such as natively produced versus recombinantly produced. Or, the neurotoxins may be a native or wild-type neurotoxin, and a modified neurotoxin.

In addition, as discussed above, the neurotoxins may be provided in compositions which include different neurotoxin stabilizers or amounts of stabilizers, or even no stabilizers.

In one specific embodiment of the foregoing method, the comparing step comprises comparing a mean depth of a skin wrinkle in proximity to the first muscle before administration of the first *botulinum* neurotoxin, and the mean depth of the skin wrinkle after administration of the first *botulinum* neurotoxin to determine an effect of the first *botulinum* neurotoxin on the depth of the skin wrinkle. Similarly, the mean depth of a skin wrinkle in proximity to the second muscle before administration of the second *botulinum* neurotoxin may be compared to the mean depth of the skin wrinkle after administration of the second *botulinum* neurotoxin to determine an effect of the second *botulinum* neurotoxin on the skin wrinkle. The effects of the first and second *botulinum* neurotoxins may then be compared.

The present methods may also comprise additional steps. For example, the present methods may comprise ultrasonically measuring muscle mass of the muscle that was administered the neurotoxin. Or, the method may comprise measuring a urodynamic effect resulting from administration of the neurotoxin or neurotoxins. Or, the methods may comprise measuring a gravimetric effect, or staining a tissue sample with starch and iodine.

*Botulinum* toxins for use according to the present invention can be pure *botulinum* toxins (e.g., the 150 kD type A toxin), can be stored in lyophilized or vacuum dried form in containers under vacuum pressure or be in a liquid format. Prior to lyophilization the *botulinum* toxin can be combined with pharmaceutically acceptable excipients, stabilizers and/or carriers, such as albumin. The lyophilized or vacuum dried material can be reconstituted with saline or water.

The present methods are not only effective in demonstrating efficacy or potency of a Clostridial neurotoxin, such as *botulinum* neurotoxin, but they are also effective in comparing and/or determining the predictability and bio-equivalence of neurotoxin potency, safety, duration of effectiveness, and antibody response. Thus, the present methods enable neurotoxins, such as *botulinum* neurotoxins to be compared within a serotype class, such as serotypes A, B, C, D, E, F, and G, among different serotype classes, and among native neurotoxins versus new formulations and/or modified neurotoxins. The present surface topographical methods for comparing multiple, such as two or more *botulinum* neurotoxins, can employ one or more of surface electromyographical (sEMG) recordings, molds, and photography, as discussed herein.

In each of the following examples, the specific amount of a *botulinum* toxin administered depends upon a variety of factors to be weighed and considered within the discretion of the attending physician and in each of the examples insignificant amounts of *botulinum* toxin enter appear systemically with no significant side effects.

As indicated above, dosages of the neurotoxin, such as *botulinum* toxin, in the compositions may vary. In one embodiment, the compositions contain a therapeutically effective amount of neurotoxin, for example, between about 1 U and about 500 U of *botulinum* toxin type A. Preferably the amounts are between about 10 U and about 300 U. More preferably the amount is between about 20 U and 250 U, such about 50 U to 200 U, or 70 U.

Alternatively, *botulinum* toxin, such as *botulinum* toxin type A, can be administered in amounts between about $10^{-3}$ U/kg and about 60 U/kg to alleviate pain experienced by an individual, such as a human patient. Preferably, the *botulinum* toxin used is administered in an amount of between about $10^{-2}$ U/kg and about 50 U/kg. More preferably, the *botulinum* toxin is administered in an amount of between about $10^{-1}$ U/kg and about 40 U/kg. Most preferably, the *botulinum* toxin is administered in an amount of between about 1 U/kg and about 30 U/kg. In a particularly preferred embodiment of the present disclosed methods, the *botulinum* toxin is administered in an amount of between about 1 U/kg and about 20 U/kg.

Compositions containing other serotypes of *botulinum* toxin may contain different dosages of the *botulinum* toxin. For example, *botulinum* toxin type B may be provided in a composition at a greater dose than a composition containing *botulinum* toxin type A. In one embodiment, *botulinum* toxin type B may be administered in an amount between about 1 U/kg and 150 U/kg. *Botulinum* toxin type B may also be administered in amounts of up to 20,000 U (mouse units, as described above). In another embodiment of the invention, *botulinum* toxin types E or F may be administered at concentrations between about 0.1 U/kg and 150 U/kg. In addition, in compositions containing more than one type of *botulinum* toxin, each type of *botulinum* toxin can be provided in a relatively smaller dose than the dose typically used for a single *botulinum* toxin serotype. The combination of *botulinum* toxin serotypes may then provide a suitable degree and duration of paralysis without an increase in diffusion of the neurotoxins (e.g. see U.S. Pat. No. 6,087,327).

EXAMPLES

The following examples set forth specific embodiments of the present invention and are not intended to be limiting examples of the scope of my invention.

Example 1

Facial Topography Method for Determining Effect of a *Botulinum* Toxin Upon Frontalis Muscle A female patient 36 years of age presents with bilateral, symmetrical and moderately severe forehead lines during maximum voluntary contraction of the frontalis muscle.

All make-up and cosmetics are removed from the patient's forehead, which is then cleansed with an alcohol solution. A silicon replica is made of the patient's right frontalis during maximum voluntary contraction of the frontalis muscle as follows. The frontalis muscle is identified by having the patient look up and elevate her eyebrows. sEMG is used to confirm frontalis contraction. An adhesive ring 2.4 cm in diameter is positioned over an injection site on the right frontalis. A thin layer of freshly prepared silicon replica mixture (rubber silicon, 2 g, and amyl acetate catalyst, 2 drops) is applied within the adhesive ring on the right side of the forehead during maximum voluntary contraction of the frontalis muscle. The patient is instructed to maintain maximal frontalis muscle contraction for four minutes in which time the silicone polymer sets. After about 5 minutes, the hardened silicon replica is removed. The skin surface replica obtained provides a baseline negative impression (a mold) and record of the skin surface to which the silicone polymer set.

A syringe containing 20 U of a *botulinum* toxin type A (such as BOTOX) is directed across the frontalis muscle fibers perpendicular to the forehead skin surface and keeping the needle-tip bevel side up, and with the frontalis at rest, 10 U of the *botulinum* toxin is injected bilaterally injections into each of the right and left frontalis muscle, at a position 2.5 cm above the superior arch of the left and right eyebrows, in line with the vertical axis of the center of the pupils. The patient is followed over a 62 week period subsequent to the injection of the *botulinum* toxin and at each visit additional right frontalis silicon replicas are made.

Figure 2:
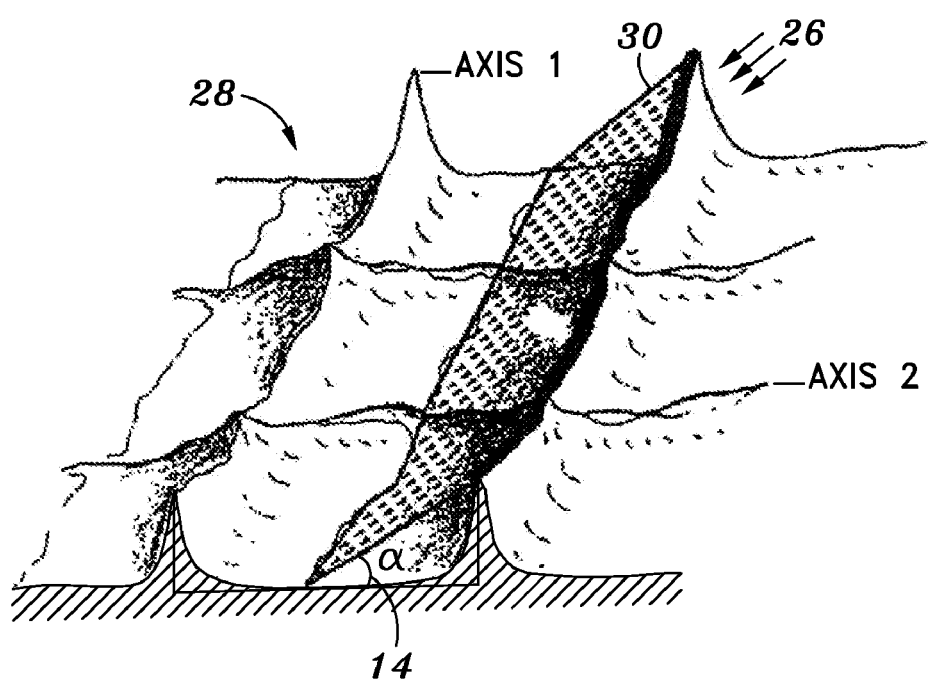
FIG. 2 is a hypothetical close up representation of a section of a skin surface replica (skin impression side of a silicone rubber mold)) made for use in a method of the present invention.

The baseline silicon replica is compared to the subsequent series of replica obtained from the patient. As shown by FIG. 1, a silicon replica 10 is placed on a horizontal surface 22 on a table 24 under a digital imaging camera 16, held up by support 18. The replica 10 is illuminated by light from a light source 12 orientated at an angle 14 (35° is a preferred angle) from the horizontal (and perpendicular to the major skin lines) thereby generating shadows due to the negative impressions of lines, wrinkles and furrows in the skin present on the replica surface, as shown by FIG. 2. In FIG. 2 the light 26 is incident upon the negative skin surface replica 28 at the angle 14. Preferably, a single light source 12 is used to illuminate the replica 10, because use of two or more light sources to illuminate a replica can prevent generation of the shadows (contrast) needed to view and examine skin surface features and characteristics. The digital camera 16 connected by means 26 to a computer 20 equipped with, for example, Quantirides software (version 2.0, Monaderm, Monaco). The Quantirides software can generate and analyze the imaged skin surface topography impression (replica), as shown by the silicon replica. One or more of the following parameters can be calculated by the software with regard to skin surface characteristics recorded by the impressions: mean depth (µm) of a skin wrinkle, mean length (mm) of a skin wrinkle, total length (mm) of skin wrinkles, total number of skin wrinkles, surface area of the skin wrinkles (depth×length; mm$^2$) and form factor (ratio mean skin wrinkle length/mean skin wrinkle depth) and used to obtain the data shown in Table 1 below. The skin wrinkles revealed by an examination of the impressions made are skin surface wrinkles. Additionally, the data obtained is only with regard to the skin surface characteristics of the skin surface area recorded by the impressions made. Thus, all of the six characteristics noted, including the total length and total number characteristics, are only with regard to the skin surface area or areas upon which the impressions are made.

Table 1 provides a sample of the data that can be obtained using the present method. Thus, the data that can be obtained on day 3 shows that the present method permits a determination that the onset of a muscle paralytic effect subsequent to administration of the *botulinum* toxin that takes place on about day 3. Additionally, as set forth by Table 1, the data that can be obtained at day 28 shows that the present method permits a determination that a peak muscle paralytic effect subsequent to administration of the *botulinum* toxin takes place at about day 28. Finally, as set forth by Table 1, the data that can be obtained at day 104 shows that the present method permits a determination that the duration of a muscle paralytic effect (i.e. recovery) subsequent to administration of the *botulinum* toxin takes place at about day 104. Thus, this example demonstrates that the facial topography method set forth in this example can be used to determine onset, peak and duration of the paralytic effect of the *botulinum* toxin upon a muscle, such as the frontalis muscle.

TABLE 1

|  | Baseline Measurement (pre-toxin injection/day 0) | Onset of Muscle Paralysis (measured at 3 days post-toxin injection) | Peak Muscle Paralysis (measured at 28 days post-toxin injection) | Recovery (Duration of Effect) from Muscle Paralysis (measured at 104 days post-toxin injection) |
|---|---|---|---|---|
| Mean Depth (µm) | 20 | 18 | 1.94 | 20 |
| Mean Length (mm) | 150 | 135 | 14.55 | 150 |
| Total Length (mm) | 175 | 157.5 | 16.97 | 175 |
| Number of wrinkles* | 8 | 7.2 | .776 | 8 |
| Surface Area of Wrinkles (mean depth × mean length; mm$^2$) | 3,000 | 2700 | 28.22 | 3,000 |
| Form Factor (ratio of mean length/mean depth) | 7.5 | 6.75 | 7.5 | 7.5 |

Example 2 sEMG Method for Determining Effect of a *Botulinum* Toxin Upon Frontalis Muscle

The patient in Example 1 has two pairs of surface EMG electrodes placed on the left and right frontalis and the monitor of the sEMG processor is placed within the patient's field of vision to enable the amplitude of the signal to be viewed by the patient and thereby assist with maintenance of maximum voluntary contraction.

Figure 3:
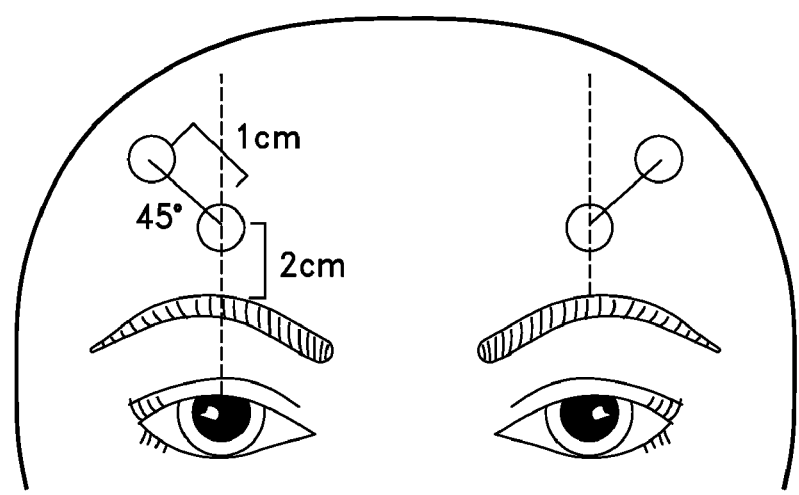
FIG. 3 is a diagrammatic illustration of a placement of surface EMG electrodes on a patient.

The first electrode is placed 2 cm above the brow in a vertical line with the pupil. The second electrode is positioned laterally to the first electrode at a 45-degree angle. The inter-mid-electrode distance is 1 cm. The second electrode is placed at a 45-degree angle to be parallel with the frontalis muscle fibers to increase recording accuracy. The 45-degree angle is measured using a protractor. The recording electrodes is trimmed for ease of inter electrode spacing. The ground electrodes are placed directly in front of each ear, in the pre-auricular area. Electrode placement is shown by FIG. 3.

Surface electromyographic quantification of the frontalis muscle activation is recorded using a Neuroeducator III Surface EMG Processor. The EMG processor has independent isolated channels, each with differential amplifiers to enhance the signal to noise ratio and minimize electrical noise and 50 Hertz (Hz) artifact interference. Muscle (electrical) activity is recorded using a continuous analog integrator, read by the processor at 100 times per second, with a passband of 10–1000 Hz, assuring wideband monitoring without loss of the muscle signal. The recorded sEMG signal is full-wave rectified, and the integrated sEMG recording is displayed on the screen and stored in both graphic and numerical forms.

The same sEMG processor and disposable self-adhesive, pre-gelled Ag—AgCl surface electrodes (1 cm in diameter recording area) are used for all measurements. The active and reference electrodes are identical disposable adhesive electrodes used to record the amplitude muscle activity during maximum voluntary contraction. A new set of electrodes can be used for each patient at each visit. Additional sets are used as required to maintain good adhesion to the skin of the patient and to minimize 50 hertz Hz noise.

The method of recording enables common mode rejection by the sEMG processor, a technique that minimizes crosstalk influences on the muscle activity recorded. Prior to application of the electrodes, the skin is cleansed with alcohol to minimize 50 Hz skin impedance. sEMG is carried out during maximum voluntary contraction of the frontalis muscle using a bipolar surface recording method and the room temperature can be maintained at approximately 20° C.

The patient is sitting in an upright relaxed position facing the sEMG monitor. This positioning can allow the patient to observe their maximum amplitude signal displayed on the monitor and assist in maintaining maximum voluntary contraction for the required duration. The patient is asked raise her eyebrows to achieve the maximum target signal and sustain it at that level for 10 seconds.

The sEMG signal obtained from the surface electrodes is processed by computer. The intensity of the responses is collected during maximum voluntary contraction of the frontalis muscle.

Surface Electromyography (sEMG) is carried out by comparing baseline sEMG studies with the results of serial sEMG studies following injection of a *botulinum* toxin into the frontalis muscle. The amplitude ($\mu V$) of the maximum voluntary contraction for the frontalis muscle is obtained by the sEMG recording. The Neuroeducator III surface EMG processor provides an integrated sEMG amplitude value (in $\mu V$) recorded from the electrodes placed on the right and left frontalis muscle. The sEMG recording decreases as the toxin begins its paralytic effect and increases as the effect of the toxin wears off.

The parameters that can be determined by the data from this sEMG analysis are onset of muscle weakness, degree of muscle weakness and recovery from muscle weakness.

Example 3

Photographic Method for Determining Effect of a *Botulinum* Toxin Upon Frontalis Muscle Photographs are taken of the patient in Example 1, following the sEMG procedure. At each visit, digital and 35 mm photographs frontal view of the patient's upper face are taken.

The patient is positioned in the same manner for all photographs. A stereotactic device is used to ensure consistent positioning of the face in relation to the camera which comprises a dedicated chin/head support assembly. In addition, the image obtained at the screening visit (day zero) is used as a reference to ensure identical positioning of the head at all subsequent visits. Following positioning of the patient and verification of the set-up of the camera, the patient is requested to maximally elevate her eyebrows (by maximum voluntary contraction of the frontalis muscle) by viewing the fixed indicator. Three exposures of the full frontal view (0°) of the upper face can then be taken with both a 35 mm and with a digital camera.

For all photographs lighting, framing and exposure ratios are held constant. Standardized magnification and aperture can also be used. For magnification a standardized reproduction ratio of 1:5 (35 mm equivalent) is used for both the digital and 35 mm facial photographs. The camera aperture for all 35 mm facial photographs is at f/16, and for all digital facial photographs the camera aperture is set at f/32.

The 35 mm photographic images are digitally scanned and analyzed in the same way as the digital photographs. All photographic images are calibrated and analyzed using both Mirror DPS (Canfield Scientific, Inc., Fairfield, N.J.) and Image Pro Plus (Media Cybernetics, Silver Spring, Md.). The software can draw a horizontal line through the inner canthus of the eyes and calculate the distance in millimeters between this line and the lower edge of the eyebrow at three specific points. Images from a patient are re-sized and adjusted to the same magnification as the baseline image using Mirror DPS, i.e. all images for a patient is identically sized. Images are then exported to Image Pro Plus and rotated such that a straight blue line intersects the inner canthus of the eyes.

A reduction in brow mobility (in mm) during maximal voluntary contraction is used to show onset, peak and duration of the paralytic effect. Photography is carried out by comparing baseline 2 dimensional digital (2D) and 35 mm image studies with results of serial 2D and 35 mm image studies following injection of the *botulinum* toxin into the frontalis muscle.

Response is determined by comparing baseline 2 dimensional digital (2D) and 35 mm image studies with results of serial 2D and 35 mm photographical image studies following injection of a Clostridial toxin into the frontalis muscle.

The reduction of the upward mobility of the eyebrow measured during maximum eyebrow elevation is obtained using the following measurement. The parameters determined by the data from this photography analysis are onset of muscle weakness, degree of muscle weakness and recovery from muscle weakness.

Example 4

Clinical Study for Determining Effect of a *Botulinum* Toxin Upon a Frontalis Muscle The therapeutic advantages of a *botulinum* toxin are widely acknowledged for the treatment of movement disorders and muscle spasm across multiple indications. The clinical response to a *botulinum* toxin following administration into a muscle is typically one of local and reversible muscle weakening and is well documented and the mechanism of toxin action as an inhibitor of acetylcholine is well understood. However, the pharmacokinetic properties of a *botulinum* toxin have been more difficult to determine. Its chemical complexity and extremely low doses due to its potency have limited the use of traditional pharmacokinetic techniques.

To understand the pharmacodynamic properties of a *botulinum* toxin, a clinical study was carried out to evaluate several methods which could objectively measure its action. The selected site of action was the frontalis muscle of the forehead. Three methods were chosen to quantify the effect of a *botulinum* toxin on the contraction of this muscle: a computerized image analysis of silicone replicas of the forehead to evaluate skin topography; surface electromyography to directly measure the electrophysiological activity of the frontalis muscle; and photographic images to quantify electronically the degree of brow elevation.

To ensure that measurable changes could be made following a *botulinum* toxin treatment (i.e. by intramuscular injection), subjects selected for the study had 'moderate' wrinkle severity on maximum voluntary contraction of the frontalis muscle and were in an age group where brow furrow is due essentially to muscle contraction as opposed to age related factors (18–40 years). Since the muscle weakening effect of a *botulinum* toxin can occur rapidly and extend over several months, the study was designed with 17 visits, 7 of which were scheduled over the first 2 weeks with the final visit at week 60. The data presented in this Example are up to and including week 24. An untreated control group was included to assess any response in the model variables when no treatment was received.

The effect of a *botulinum* toxin was demonstrated in all 3 models over the 24 week period. Five key and relevant variables were identified on the basis of clinical relevance and consistency of results. These were mean and maximum wrinkle depth (topography), mean AUC (surface electromyography) and centre line distance to eyebrow and the average distance of all variables to eyebrow (photography). The consistent pattern of change observed for the above variables was further demonstrated by the correlation of mean values from one variable with the mean values of another variable.

For these key variables, statistically significant differences were seen in mean change from baseline and from placebo in all the *botulinum* toxin treated groups, with no notable changes in either the placebo or untreated control groups. The magnitude of change was greatest in the 20 U (U=unit) *botulinum* toxin group and although pairwise tests showed some differences between the 20 U and the lower dose groups, there were no consistent differences between the 10 U and 5 U groups, except for the photography model. Statistically significant within group and among group changes were observed highlighting the sensitivity of the model and presence of a strong treatment effect.

The photography variables, distance from centre line to eyebrow and the average distance of all variables to eyebrow, showed consistent changes in response to the *botulinum* toxin. As known, the largest displacement when raising the eyebrow occurs at the centre of the brow as compared to the inner or outer edges. Brow mobility in the present study decreased by a maximum of 6.8 mm from baseline (−25%, day 11) at the centre line compared to 4.9 mm and 4.2 mm at the inner and outer edges, respectively, following a dose of 20 U of the *botulinum* toxin.

Thus, five key and clinically relevant variables were identified that demonstrated a consistent pattern of change over the 24 week study period following injection of a *botulinum* toxin as 5 U, 10 U or 20 U into the frontalis muscle. For mean and maximum wrinkle depth (topography), mean AUC (surface electromyography) and centre line distance to eyebrow and the average distance of all variables to eyebrow (photography), statistically significant within group changes from baseline and among group differences from placebo were observed for all 3 of the *botulinum* toxin treatment groups.

Onset, peak and duration of effect were consistent in the *botulinum* toxin treated groups for the 5 key variables across the models. Onset of effect occurred between days 1–4 and time of peak effect occurred between days 9 and 14.

The details of the clinical study carried out are as follows. A double-blind, randomized, placebo-controlled, parallel group clinical study was carried out, with an untreated control group, to evaluate the safety and the topographical, electrophysiological and photographical responses of the frontalis muscle to varying doses of intramuscularly injected BOTOX® (*Botulinum* Toxin, Type A) Purified Neurotoxin Complex, in healthy volunteers.

Active groups received BOTOX® at 5 units, 10 units, or 20 units and were followed for 24 weeks and are planned to be followed for a total of 62 weeks.

Subjects were randomly assigned to receive a treatment of either, BOTOX® at a total dose of 5 U, 10 U, 20 U or placebo or no treatment (single-blind untreated control group) in 1:1:1:1:1 ratio.

Visit Schedule: Day-14 to day-7 (screening), day 0 (randomization and treatment), days 1, 2, 4, 6, 9, 11, 14 and weeks 4, 8, 12, 16, 20, 24, 36, and 60 (follow-up topography, sEMG and photography). 61 subjects were enrolled (12 in BOTOX® 5 U, 11 in BOTOX® 10 U, 13 in BOTOX® 20 U, 13 in placebo, 12 in untreated control group). 61 subjects completed the week 24 visit.

The subjects were all healthy volunteers (male or female 18–40 years of age) with bilateral, symmetrical and at least 'moderate' forehead lines during maximum voluntary contraction of the frontalis muscle on a scale of none, mild, moderate, severe.

The test product used was BOTOX® reconstituted with 0.9% sterile nonpreserved saline and administered as a single treatment of bilateral intramuscular injections in the right and left frontalis muscle. Each of the 2 injections was 0.1 mL containing BOTOX® 2.5 U, 5 U or 10 U, for a total dose of BOTOX® 5 U, 10 U or 20 U. A single treatment (injection) was applied at day 0 with follow-up for 60 weeks (24 weeks of data are presented) herein.

The placebo was the BOTOX® vehicle reconstituted and injected in an identical way to the test product. In addition, the untreated control group (not injected) was followed in an identical way to both the active and placebo groups.

Criteria for Evaluation:

Efficacy: the primary assessments were based on response variables in 3 models.

Topography: mean depth, maximum depth, mean length, total length and number of wrinkles and surface area of wrinkles at maximum voluntary contraction of the frontalis muscle.

Surface Electromyography (sEMG): amplitude (μV) of response measured at maximum voluntary contraction of the frontalis muscle. Mean area under curve (AUC) and mean contraction response were derived.

Photography: 3 measurements (cm) taken from a fixed horizontal line intersecting the inner canthus of both eyes to 3 points on the lower edge of the eyebrow, to determine the reduction in the upward mobility of the eyebrow during maximum eyebrow elevation. Measurements were taken using 2 dimensional (2D) digital and 35 mm photographic images.

Onset, peak and duration of effect were derived from the topography, sEMG and photography variables.

Statistical Methods:

Three exploratory analyses were planned: an interim analysis on data up to and including week 4, the primary analysis on data collected up to and including week 24 (presented herein); the secondary analysis on data up to and including week 60 (in process). Three populations were used in the analyses: the intent-to-treat (ITT), per protocol (PP) and safety populations, except for the interim analysis where the only ITT population was used.

The primary efficacy analyses were based on mean change and mean percent change from baseline for topography, sEMG and photography variables at week 24 for the ITT population using a one-way analysis of variance (ANOVA). Pairwise comparisons versus placebo were performed using a t-test. Summary statistics of response profile over time for each treatment group were planned to estimate the onset, peak and duration of effect. If between-group differences were observed for covariates, an analysis of covariance (ANCOVA) model was planned to determine other factors which may have affected the outcome. Concomitant medications were summarized by therapeutic class and drug name. The null hypothesis was tested at the 0.05 level.

The primary analysis was replicated on mean change and mean percent change from baseline for the efficacy variables using the PP population. For the sEMG data, a secondary analysis was performed on the mean AUC change and percent change from baseline for the 3 curves collected from the right and left frontalis muscle. This analysis will be repeated at week 60.

All safety analyses were performed on the safety population. A Pearson's chi-squared test was used to test for differences between the treatment, placebo and untreated control groups.

Summary 61 subjects enrolled (12 in the BOTOX® 5 U, 11 in the BOTOX® 10 U, 13 in the BOTOX® 20 U, 13 in the placebo and 12 in the untreated control group). No subjects discontinued from the study between day 0 and week 24. Mean age was 32 years, with 70.5% of subjects aged ≧30 years. A total of 50.8% of subjects were female and 49.2% males. The majority of subjects were Caucasian (96.7%).

In general, regardless of the clinical pharmacology model used, all 3 BOTOX® treatment groups showed statistically significant within-group mean changes from baseline and mean percent changes from baseline. Five key variables showed a clear and clinically relevant pattern of change over the 24-week study period: mean wrinkle depth and maximum wrinkle depth (topography model), mean AUC (sEMG model), distance of centre line to eyebrow and average distance of all variables to eyebrow (photography model).

Statistically significant differences from placebo were observed in all 3 BOTOX® treatment groups. Overall, there were no significant between-group differences between the untreated control group and placebo.

A consistent pattern of change was seen with respect to onset, peak and duration of effect in the BOTOX®-treated groups. Overall, onset of effect occurred between days 1–4, peak time of effect occurred between days 9 and 14, and duration of effect currently appears to be longest in the 20 U BOTOX® group, continuing up to weeks 16–24, with a shorter duration in the 5 U (weeks 8–24) and 10 U BOTOX® groups (weeks 8–24).

Magnitude of effect was generally greater in the 20 U group compared to the lower dose groups. Pairwise analyses of the BOTOX®-treated groups showed, for some variables, statistically significant differences between the 20 U and 10 U groups and between the 20 U and 5 U groups at some visits although no consistent or significant differences in effect were observed between the 5 U and 10 U groups except for some variables in the photographic model.

Regression analyses confirmed the primary analyses demonstrating an effect of BOTOX® versus placebo. No clinically relevant changes in vital signs were seen during the study.

Conclusion

Five key and clinically relevant variables were identified that demonstrated a consistent pattern of change over the 24 week study period following injection of BOTOX® 5 U, 10 U or 20 U into the frontalis muscle.

For mean and maximum wrinkle depth (topography), mean AUC (surface electromyography) and centre line distance to eyebrow and the average distance of all variables to eyebrow (photography), statistically significant within-group changes from baseline and among-group differences from placebo were observed for all 3 BOTOX® treatment groups.

Onset, peak and duration of effect were consistent in the BOTOX-treated groups for the 5 key variables across the models. Onset of effect occurred between days 1–4 and time of peak effect occurred between days 9 and 14.

Example 5

Surface Topographical Methods for Comparing botulinum Toxin Type A Obtained from Different Strains of Bacteria The methods of Example 4 can be repeated. However, the people are grouped into two groups. The first group receives 20 U of BOTOX®, and the second group receives 20 U of DYSPORT®. The effects of the administration of the compositions are monitored over time, as described in Example 4, and the effects are compared between the two compositions. The first group of people show a greater reduction in wrinkle depth and wrinkle length compared to the second group. However, both groups demonstrate a reduction in wrinkles for about 4 months.

Example 6

Surface Topographical Methods for Comparing botulinum Toxin Type A and botulinum Toxin Type B The methods of Example 4 can be repeated. The people are grouped into two groups. The first group receives 20 U of BOTOX®, and the second group receives 20 U of MYOBLOC®. Both groups are administered botulinum toxin to the left frontalis muscle. The effects of the administration of the compositions are monitored over time, and are compared between the two compositions. The first group of people show a greater reduction in wrinkle depth and wrinkle length compared to the second group. Indeed, the second group show almost no reduction in wrinkles.

The methods are repeated except the second group is administered 200 U of MYOBLOC®. A proportion of the second group exhibits some wrinkle reduction, and considerably less wrinkle reduction than the first group that received BOTOX®.

Example 7

Surface Topographical Methods for Comparing Different Serotypes of botulinum Toxins Example 6 is repeated except that 20 U of one of botulinum toxin types C, D, E, F, or G is administered to the second group of people instead of 20 U of MYOBLOC®. In follow up studies, increased dosages of *botulinum* toxin types C, D, E, F, and G are administered to the patients, and the wrinkle reduction effects, if any, are compared to the effects caused by administration of BOTOX®.

Example 8

Surface Topographical Methods for Comparing *botulinum* Toxin-Containing Compositions with Different Stabilizers The methods of Example 4 are repeated. The first group of people receive BOTOX®. The second group of people is administered a composition comprising *botulinum* toxin type A and hetastarch. The third group of people is administered a composition comprising a *botulinum* toxin type A and a recombinant albumin. The fourth group of people is administered a composition comprising a *botulinum* toxin type A and gelatin. The fifth group is administered a purified *botulinum* toxin type A without a stabilizer. The wrinkle reduction effects are monitored over time. The effects are compared for the various compositions. Differences in the effects among the compositions correspond to differences in effectiveness of the *botulinum* toxin which may be due to the presence of different stabilizers.

Example 9

Surface Topographical Methods for Comparing *botulinum* Toxin-Containing Compositions at Different Times The methods of Example 4 are repeated. The patients are administered 20 U of BOTOX. Eight months later (after the effects of BOTOX have worn off), the patients are administered 20 U of MYOBLOC in the same location. The wrinkle reducing effects caused by BOTOX are compared to the wrinkle reducing effects caused by MYOBLOC by comparing molds, sEMG records, and photographs of the patients.

Example 10

Surface Topographical Methods for Comparing *botulinum* Toxin-Containing Compositions Bilaterally Administered Patients are administered 40 U of BOTOX to the left frontalis muscle, and are administered 40 U of MYOBLOC to the right frontalis muscle, as described in Example 4. The wrinkle reduction effects are monitored for six months. The effects are compared by examining molds for the left and right frontalis muscles, examining sEMG records for the left and right frontalis muscles, and examining photographs of the left and right frontalis muscles.

Although the present invention has been described in detail with regard to certain preferred methods, other embodiments, versions, and modifications within the scope of the present invention are possible. For example, a wide variety of skin muscles can be injected and their overlying or adjacent skin surface areas examined by the disclosed method. All patents and publications cited herein are incorporated by reference in their entireties.

Accordingly, the spirit and scope of the following claims should not be limited to the descriptions of the embodiments of my invention set forth above.

What is claimed is:

1. A method for comparing *botulinum* neurotoxin-containing compositions, comprising the steps of:
    examining a first superficial body region and a second superficial body region of an individual, the first and second superficial body regions comprising at least a portion of a muscle, wherein the first superficial body region and the second superficial body region are examined while the muscle is at a maximum voluntary contraction;
    administering a first *botulinum* neurotoxin-containing composition to the first region;
    administering a second *botulinum* neurotoxin-containing composition to the second region;
    and examining the first superficial body region after administration of the first composition while the muscle of the first superficial body region is at a maximum voluntary contraction to determine an effect of the first composition on the first superficial body region;
    examining the second superficial body region after administration of the second composition while the muscle of the second superficial body region is at a maximum voluntary contraction to determine an effect of the second composition on the second superficial body region,
    wherein a difference in the effects corresponds to a difference in the first composition and the second composition.

2. The method of claim 1, wherein the *botulinum* neurotoxin of the first composition is different from the *botulinum* neurotoxin of the second composition.

3. The method of claim 1, wherein the *botulinum* neurotoxin of the first composition is a *botulinum* neurotoxin selected from the group consisting of *botulinum* neurotoxin types A, B, C, D, E, F, and G, and wherein the *botulinum* neurotoxin of the second composition is a *botulinum* neurotoxin other than the *botulinum* neurotoxin of the first composition.

4. The method of claim 1, wherein the *botulinum* neurotoxin of the first composition is a *botulinum* neurotoxin produced by a first strain of a Clostridial bacteria, and the *botulinum* neurotoxin of the second composition is a *botulinum* neurotoxin produced by a strain of Clostridial bacterial other than the first strain.

5. The method of claim 1, wherein the *botulinum* neurotoxin of the first composition is *botulinum* neurotoxin type A, and the *botulinum* neurotoxin of the second composition is *botulinum* neurotoxin type B.

6. The method of claim 1, wherein the *botulinum* neurotoxin of the first composition is a native *botulinum* neurotoxin obtained from Clostridial bacteria, and the *botulinum* neurotoxin of the second composition is a modified *botulinum* neurotoxin.

7. The method of claim 1, wherein the first composition comprises a polysaccharide in an amount effective to stabilize the *botulinum* neurotoxin, and the second composition is substantially free of the polysaceharide.

8. The method of claim 1, wherein the first composition comprises a recombinant albumin in an amount effective to stabilize the botulmum neurotoxin, and the second composition is substantially free of recombinant albumin.

9. The method of claim 1, wherein the first composition comprises gelatin in an amount effective in stabilizing the *botulinum* neurotoxin., and the second composition is substantially free of gelatin.

10. The method of claim 1, wherein the first composition comprises human serum albumin in an amount effective in stabilizing the *botulinum* neurotoxin, and the second composition comprises a stabilizer other than human serum albumin.

11. The method of claim 1, wherein the examining steps comprise at least one of (i) evaluating skin topography of the first and second regions; (ii) evaluating a surface electromyograph recording of the first and second regions; and (iii) evaluating photographs of the first and second regions.

12. The method of claim 11, wherein the examining steps comprise (i) evaluating skin topography of the first and second regions; (ii) evaluating a surface electromyograph recording of the first and second regions; and (iii) evaluating photographs of the first and second regions.

13. The method of claim 11, wherein the step of evaluating skin topography comprises producing an impression of the skin topography of the first and second regions before administration of the first and second compositions, respectively, and producing an impression of the skin topography of the first and second regions after administration of the first and second compositions, respectively.

14. The method of claim 1, wherein a difference in effects corresponds to a difference in the first composition and the second composition selected from one or more of the group consisting of *botulinum* neurotoxin potency, safety, duration of effectiveness, and antibody response.

15. The method of claim 1, further comprising at least one step selected from the group consisting of: ultrasonically measuring muscle mass; measuring a urodynamic effect resulting from administration of the first and second compositions; measuring a gravimetric effect; and staining a tissue sample with starch and iodine.

16. The method of claim 1 wherein the first and second compositions differ from one another other than the number of units of toxin administered to said first and second regions.

17. The method of claim 1, further comprising at least one step selected from the group consisting of: ultrasonically measuring muscle mass; measuring a gravimetric effect; and staining a tissue sample with starch and iodine.

18. The method of claim 1, further comprising at least one step selected from the group consisting of: ultrasonically measuring muscle mass; and staining a tissue sample with starch and iodine.

19. The method of claim 1, further comprising staining a tissue sample with starch and iodine.

* * * * *